(12) United States Patent
Shue et al.

(10) Patent No.: US 6,743,199 B2
(45) Date of Patent: Jun. 1, 2004

(54) DISPOSABLE SYRINGE

(76) Inventors: Ming-Jeng Shue, No. 14, Lane 8, Chung-I St., Hsi Dist., Taichung City (TW); Deborah Huang, 7F, No. 5, Sec. 3, Liu-Chun E. St., Chung Dist., Taichung City (TW)

( * ) Notice: Subject to any disclaimer, the term of this patent is extended or adjusted under 35 U.S.C. 154(b) by 9 days.

(21) Appl. No.: 10/288,780

(22) Filed: Nov. 5, 2002

(65) Prior Publication Data

US 2004/0015129 A1 Jan. 22, 2004

(30) Foreign Application Priority Data

Jul. 17, 2002 (TW) .................................. 091115946 A

(51) Int. Cl.[7] .......................... A61M 5/00; A61M 5/31; A61M 5/32; A61M 5/315
(52) U.S. Cl. ..................... 604/110; 604/192; 604/218; 604/240; 128/919
(58) Field of Search .............................. 604/93.01, 110, 604/181, 187, 192, 198, 218, 228, 231, 236, 237, 238, 240, 244, 264, 265, 905, 907; 128/919

(56) References Cited

U.S. PATENT DOCUMENTS

| | | | | |
|---|---|---|---|---|
| 5,125,898 A | * | 6/1992 | Kaufhold et al. | 604/110 |
| 5,395,337 A | * | 3/1995 | Clemens et al. | 604/110 |
| 6,413,236 B1 | * | 7/2002 | Van Dyke | 604/110 |
| 6,572,565 B2 | * | 6/2003 | Daley et al. | 600/573 |

* cited by examiner

Primary Examiner—Brian L. Casler
Assistant Examiner—Mark K. Han
(74) Attorney, Agent, or Firm—Townsend and Townsend and Crew, LLP

(57) ABSTRACT

A disposable syringe includes a tubular barrier member retained in a rear passageway of a barrel. A tubular needle seat for fixing a needle cannula is retained on the barrier member, and abuts against an abutment wall in the front passageway of the barrel while the needle cannula is disposed outwardly of the barrel. A plunger is slidable in the rear passageway, and has a seal member to seal a cavity confined in a plunger body and containing a fluid at a reduced pressure. When a pushing force applied to the plunger body moves the barrier member against the first and second frictional forces, the needle seat is released, and the seal member is ruptured, so that the needle seat and the needle cannula are suctioned into the cavity due to the pressure difference between the ambient atmosphere and the reduced pressure.

20 Claims, 21 Drawing Sheets

DISPOSABLE SYRINGE

BACKGROUND OF THE INVENTION

1. Field of the Invention

This invention relates to a disposable syringe, more particularly to a disposable syringe which enables a needle cannula to be retracted within a plunger cavity having a reduced pressure therein.

2. Description of the Related Art

Referring to FIGS. 1 and 2, U.S. Pat. No. 5,176,640 discloses a hypodermic injection syringe 10 which includes a barrel 11, a base 12 fixed to an open front end 111 of the barrel 11, a needle cannula 13 having a rear needle end 132 that extends into the barrel 11 through the base 12 along an axis and that has an engagement recess 131, and a plunger 18 slidable within the barrel 11. The plunger 18 includes a hollow shaft 14 with a vacuum chamber 141, and a head which has an elastic rubber ring 16 with a channel that is closed by a disc 161, and a plug 15 with a tube forcibly inserted into the channel of the ring 16 and secured to the shaft 14. A piston 17 is slidable in a sealed manner within the chamber 141, and is provided with an engaging rod 172 formed with an elastic flap 171 on a front end thereof.

In use, when the plunger 18 is about to finish its injection stroke, the disc 161 is lacerated by the rear needle end 132, the rod 172 then engages the needle 13 by engagement of the flap 171 and the engagement recess 131. In this state, under the action of vacuum present in the chamber 141, the rod 172 and the needle 13 are sucked into the chamber 141.

Since the needle 13 can be retained in the chamber 141 of the plunger 18 for safety disposal, the following drawbacks arise:

1. The laceration of the disc 161 may occur when the injection procedure of the syringe 10 is not finished. Thus, some medicine or blood may will remain within the barrel 11 to result in contamination.
2. In order to smoothly suck the needle 13 into the chamber 141, the securing of the needle 13 to the base 12 cannot be very tight. However, insufficient securing of the needle 13 will result in movement or removal of the needle 13 during the injection procedure.

SUMMARY OF THE INVENTION

The object of the present invention is to provide a disposable syringe which can prevent trapping of medicine or blood therein after injection and which can be operated easily and smoothly to retract a used needle within a plunger.

According to this invention, the disposable syringe includes a needle cannula, a barrel, a tubular barrier member, a tubular needle seat, and a plunger. The barrel has an inner surrounding barrel wall surface surrounding an axis and confining a passage with opposite rearward and forward openings. The inner surrounding barrel wall surface includes a larger-diameter segment and a smaller-diameter segment which confine rear and front passageways, respectively, to form a surrounding shoulder portion therebetween. The smaller-diameter segment includes a smaller front surrounding region and a larger rear surrounding region to form a surrounding abutment wall therebetween. The larger-diameter segment includes proximate and distal surrounding regions respectively proximate to and distal from the surrounding shoulder portion. The proximate surrounding region has a retaining area spaced apart from the surrounding shoulder portion.

The tubular barrier member includes front and rear surrounding edge portions, and inner and outer barrier wall surfaces. The outer barrier wall surface is retained at the retaining area by virtue of a first frictional force generated therebetween while in water-tight engagement with the proximate surrounding region, thereby partitioning the rear passageway into a compressible chamber confronting the surrounding shoulder portion, and an accommodation chamber confronting the rear surrounding edge portion. The inner barrier wall surface has a grip segment.

The tubular needle seat includes a hub portion disposed to fix the needle cannula therein. The hub portion has a surrounding front end wall, a surrounding gripped portion and an anchoring portion. The surrounding gripped portion is retained at the grip segment by virtue of a second frictional force generated therebetween when the surrounding front end wall abuts against the surrounding abutment wall and when the needle cannula is disposed outwardly of the forward opening.

The plunger is movable in the accommodation chamber, and includes a plunger body and a seal member. The plunger body includes a top end wall disposed movably to abut against the rear surrounding edge portion of the tubular barrier member, and a bottom end wall extending outwardly of the rearward opening so as to be manually operable. The top end wall has an inner peripheral edge portion surrounding the axis to define a cavity therein. The cavity extends along the axis and towards the bottom end wall to contain a fluid at a reduced pressure. The seal member is disposed to be sealingly attached to the inner peripheral edge portion along a sealing line so as to trap the fluid in the cavity.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
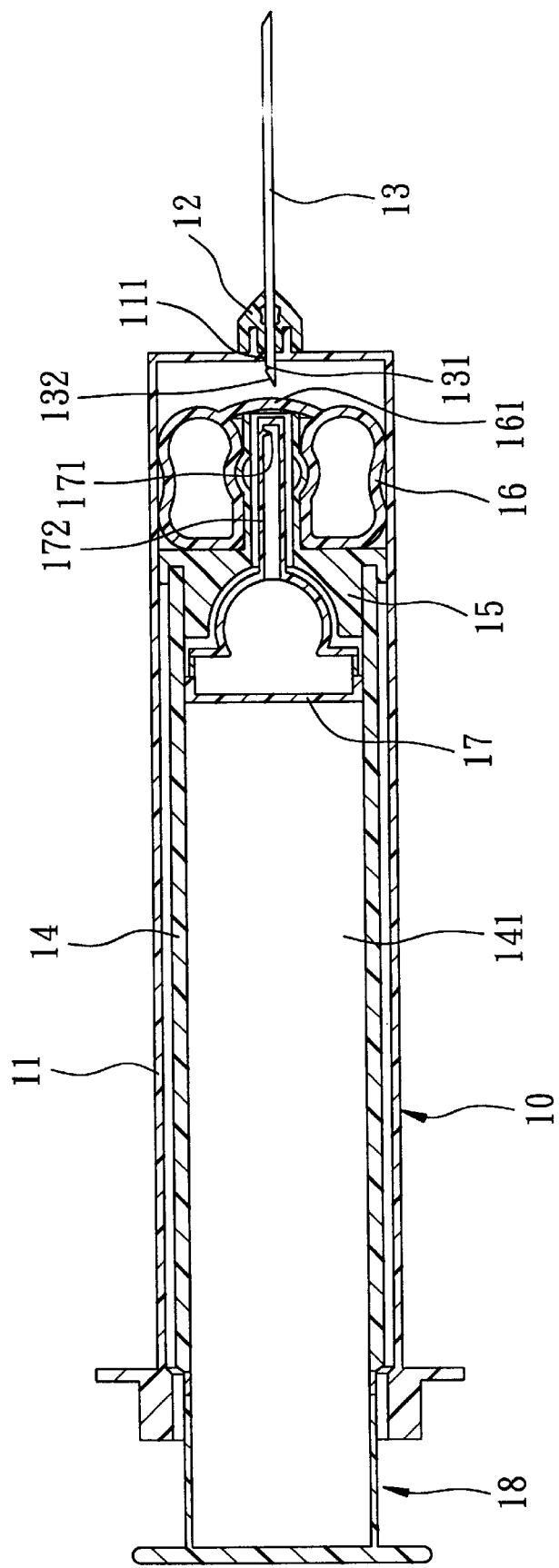
FIG. 1 is a sectional view of a conventional disposable syringe during use.
Figure 2:
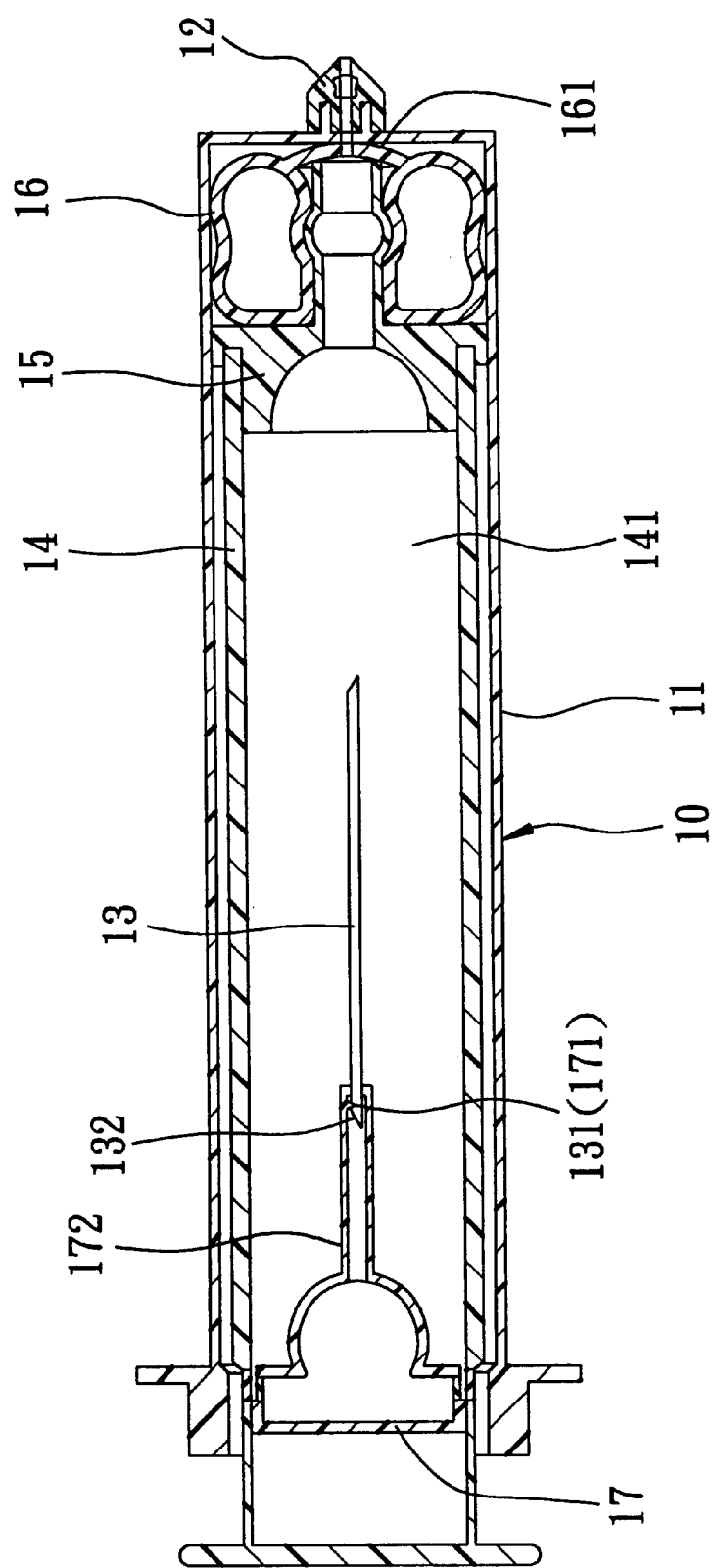
FIG. 2 shows the conventional disposable syringe of FIG. 1 after use, showing a needle cannula in a retracted state.

Before the present invention is described in greater detail, it should be noted that same reference numerals have been used to denote like elements throughout the specification.

Figure 3:
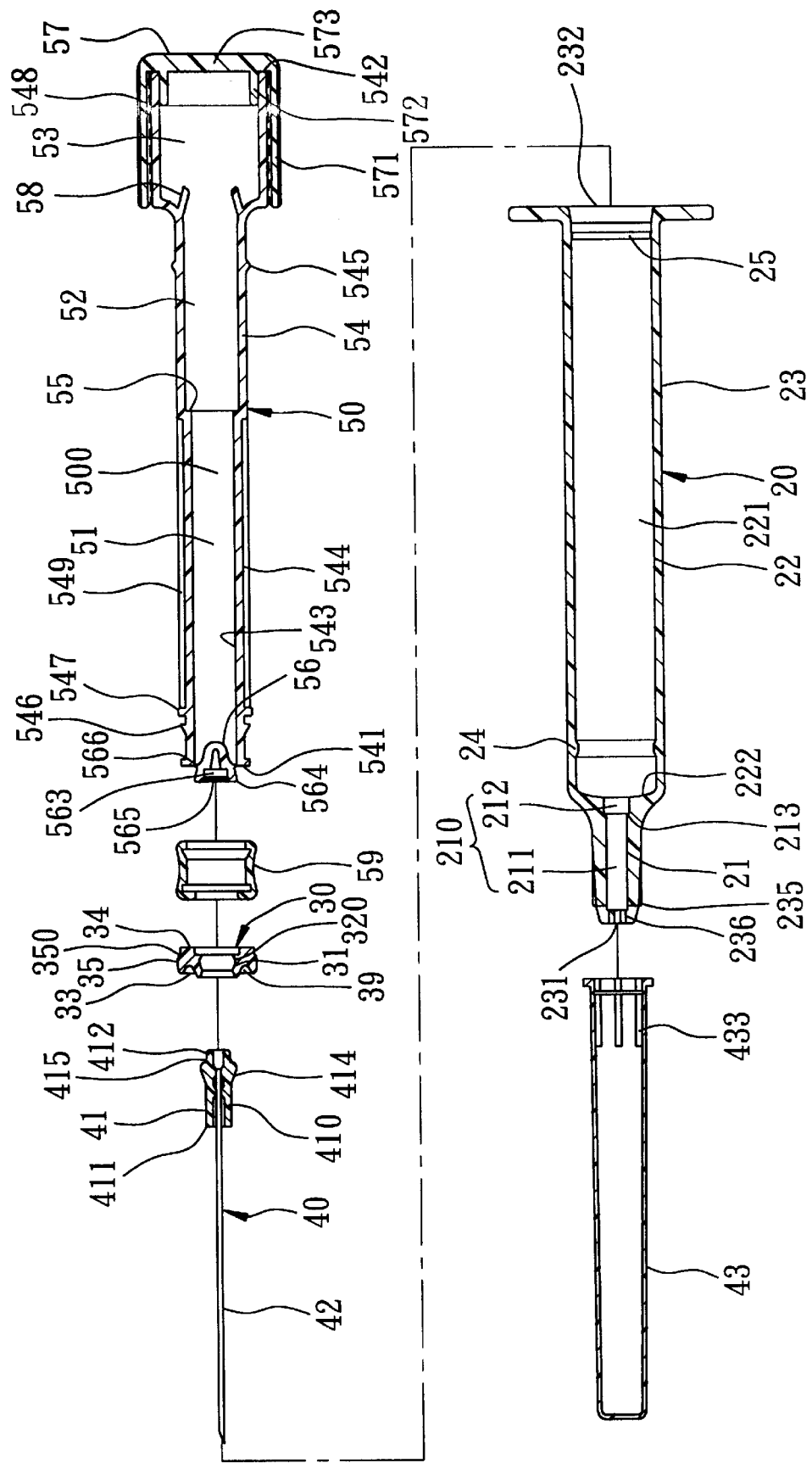
FIG. 3 is an exploded sectional view of a first preferred embodiment of a disposable syringe according to this invention.
Figure 4:
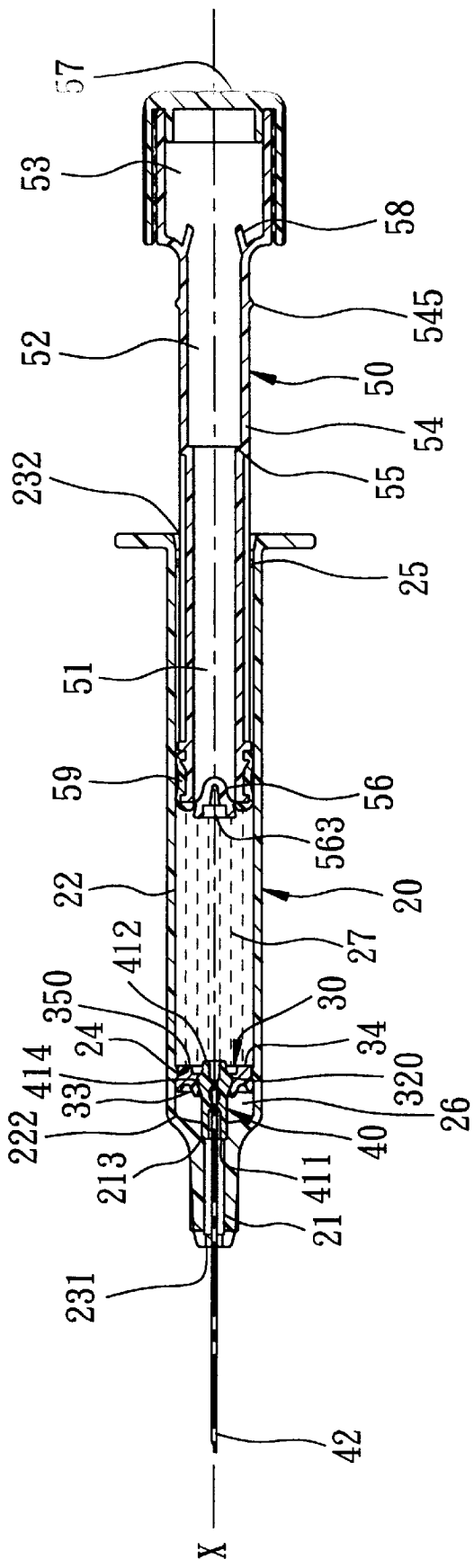
FIG. 4 is a sectional view of the first preferred embodiment during use.
Figure 5:
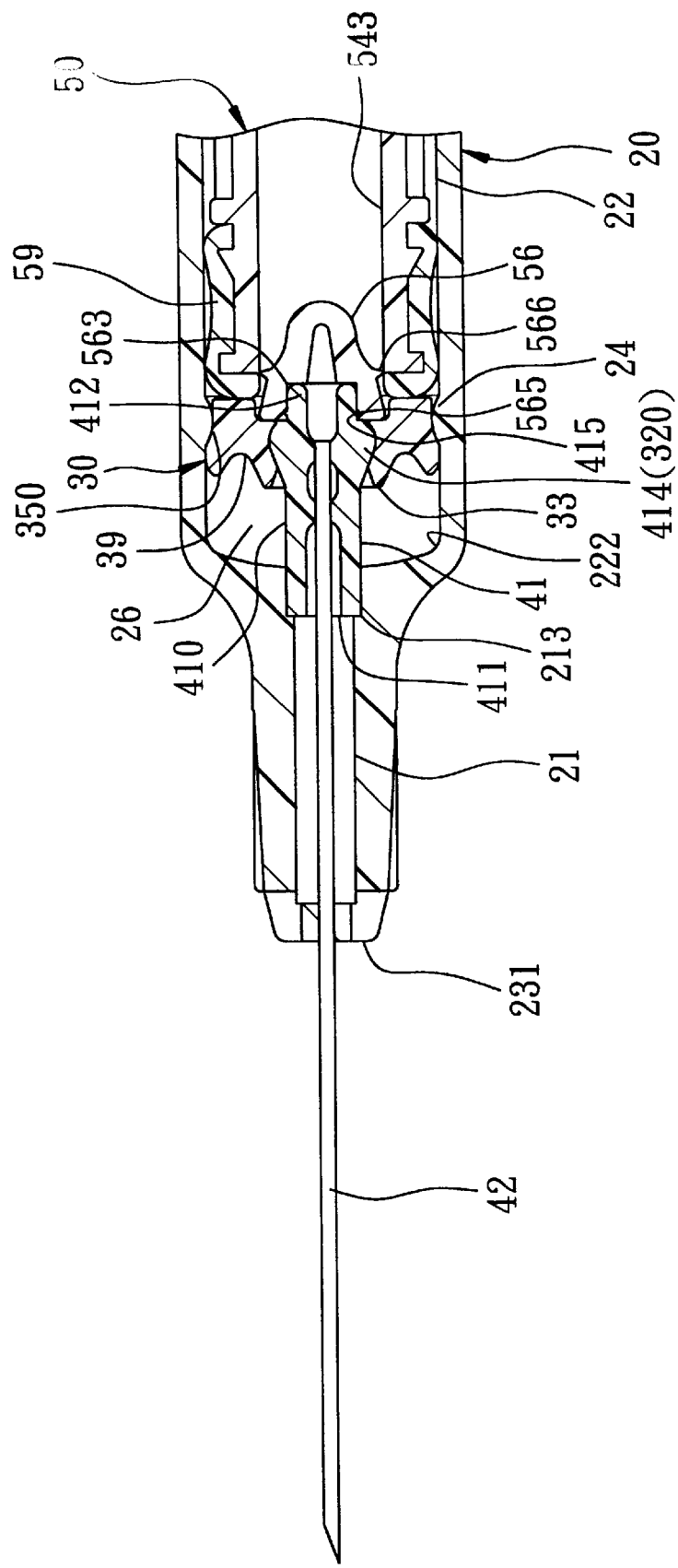
FIG. 5 is a sectional view showing a portion of the first preferred embodiment in detail.

Referring to FIGS. 3, 4 and 5, the first preferred embodiment of the disposable syringe according to the present invention is shown to comprise a barrel 20, a tubular barrier member 30, a plunger 50, and a needle assembly 40 including a needle cannula 42, a tubular needle seat 41 and a tip protector 43.

The barrel 20 has an inner surrounding barrel wall surface which surrounds an axis (X) and which confines a passage. The passage has rearward and forward openings 232,231 which are disposed opposite to each other in a longitudinal direction parallel to the axis (X). The inner surrounding barrel wall surface includes a larger-diameter segment 22 and a smaller-diameter segment 21 which confine rear and front passageways 221,210, respectively, and which are disposed proximate to the rearward and forward openings 232,231, respectively, to form a surrounding shoulder portion 222 therebetween. The smaller-diameter segment 21 includes a front surrounding region 211, and a rear surrounding region 212 which is proximate to the surrounding shoulder portion 222 and which is of a larger dimension than that of the front surrounding region 211 so as to form a surrounding abutment wall 213 therebetween. The larger-diameter segment 22 includes proximate and distal surrounding regions opposite to each other in the longitudinal direction and respectively proximate to and distal from the surrounding shoulder portion 222. The proximate surrounding region has a retaining area which is spaced apart from the surrounding shoulder portion 222 in the longitudinal direction. In this embodiment, an annular first retaining protrusion 24 is formed on the proximate surrounding region in the retaining area. An annular injection limiting protrusion 25 is formed on the distal surrounding region adjacent to the rearward opening 232. An outer surrounding barrel wall surface 23 of the barrel 20 has a rib portion 235 which extends in the longitudinal direction and which is disposed at the front surrounding region 211 adjacent to the forward opening 231.

The tubular barrier member 30 includes front and rear surrounding edge portions 33,34 opposite to each other in the longitudinal direction and which includes inner and outer barrier wall surfaces 31,35 opposite to each other and surrounding the axis (X). The outer barrier wall surface 35 is formed with an annular first retaining groove 350 such that in a position of use, the first retaining protrusion 24 is retained in the first retaining groove 350 in a water-tight manner so as to generate a first frictional force therebetween, thereby partitioning the rear passageway 221 into a compressible chamber 26 which confronts the surrounding shoulder portion 222, and an accommodation chamber 27 which confronts the rear surrounding edge portion 34. The inner barrier wall surface 31 has a second retaining groove 320 which serves as a grip segment. As shown in FIG. 5, the front surrounding edge portion 33 has a surrounding groove 39 surrounding the axis (X) such that the inner barrier wall surface 31 is more deformable in radial directions relative to the axis (X). In addition, the inner barrier wall surface 31 is divergent from the second retaining groove 320 to the front surrounding edge portion 33 so as to prevent friction contact between the inner barrier wall surface 31 and the hub portion 410.

The tubular needle seat 41 includes a hub portion 410 which is disposed to fix the needle cannula 42 therein, and which has a surrounding front end wall 411 that extends radially relative to the axis (X). An annular second retaining protrusion 414 extends from the hub portion 410 in the longitudinal direction and away from the surrounding front end wall 411 to form a surrounding gripped portion, which is retained in the second retaining groove 320 to generate a second frictional force when the surrounding front end wall 411 abuts against the surrounding abutment wall 213 and when the needle cannula 42 is disposed outwardly of the forward opening 231. An anchoring portion 412 extends from the second retaining protrusion 414 in the longitudinal direction and away from the hub portion 410, and has an annular third retaining protrusion 415 formed thereon (see FIG. 5).

The tip protector 43 has a sleeve end 433 which is disposed to sleeve on the outer surrounding barrel wall surface 23. The sleeve end 433 includes a groove portion which mates with the rib portion 235 to result in a splined engagement between the tip protector 43 and the outer surrounding barrel wall surface 23, thereby ensuring secure shielding of the needle cannula 42. Moreover, as the sleeve end 433 of the tip protector 43 is provided with the groove portion to engage the rib portion 235 on the outer surrounding barrel wall surface 23, the sleeve end 433 has a relatively large inner diameter, thereby enhancing safety during sleeving of the tip protector 43 onto the outer surrounding barrel wall surface 23.

The plunger 50 is disposed to be slidable in the accommodation chamber 27, and includes a plunger body 54, an end cap 57, and a seal member 56.

The plunger body 54 includes an open top end wall 541 which is disposed movably to abut against the rear surrounding edge portion 34 of the tubular barrier member 30, and an open bottom end wall 542 which is disposed opposite to the top end wall 541 in the longitudinal direction and which extends outwardly of the rearward opening 232. The plunger body 54 has an inner peripheral edge portion 543 which surrounds the axis (X) and which defines a cavity 500 therein. The cavity 500 extends along the axis (X) from the top end wall 541 to the bottom end wall 542 to contain a fluid at a reduced pressure. Preferably, the cavity 500 is in a substantially vacuum state. In this embodiment, the cavity 500 includes a smaller-diameter front cavity segment 51 and a larger-diameter rear cavity segment 52 which are disposed proximate to the top and bottom end walls 541,542, respectively, to form a shoulder portion 55 therebetween. Preferably, an enlarged cavity segment 53 is disposed rearwardly of the rear cavity segment 52 and outwardly of the rearward opening 232 so as to be manually operable. A plurality of rib plates 549 are formed on an outer peripheral wall surface 544 of the plunger body 54 at the front cavity segment 51, and are flush with the outer peripheral wall surface 544 at the rear cavity segment 52. An annular injection limiting protrusion 545 is formed on the outer peripheral wall surface 544 at the rear cavity segment 52 adjacent to the enlarged cavity segment 53, and is disposed to abut against the injection limiting protrusion 25 when the top end wall 541 reaches the rear surrounding edge portion 34 so as to indicate completion of an injection course.

Moreover, an annular anchoring protrusion 546 and an annular retaining flange 547 are formed adjacent to the top end wall 541. A surrounding sealing ring 59 is made of a deformable material, and is sleeved retainingly over the outer peripheral wall surface 544 adjacent to the top end wall 541 by means of the anchoring protrusion 546 and the retaining flange 547.

The end cap 57 includes an outer surrounding wall 571 which engages threadedly a threaded segment 548 of the outer peripheral wall surface 544, an inner surrounding wall 572 which is attached to the inner peripheral edge portion 543, and an end cap wall 573 which is connected to the outer and inner surrounding walls 571,572 and which covers an opening in the bottom end wall 542 in an air-tight sealing manner.

A plurality of barrier ribs 58 are formed between the rear cavity segment 52 and the enlarged cavity segment 53. Each barrier rib 58 extends from the inner peripheral edge portion 543 radially and toward the axis (X).

Figure 21:
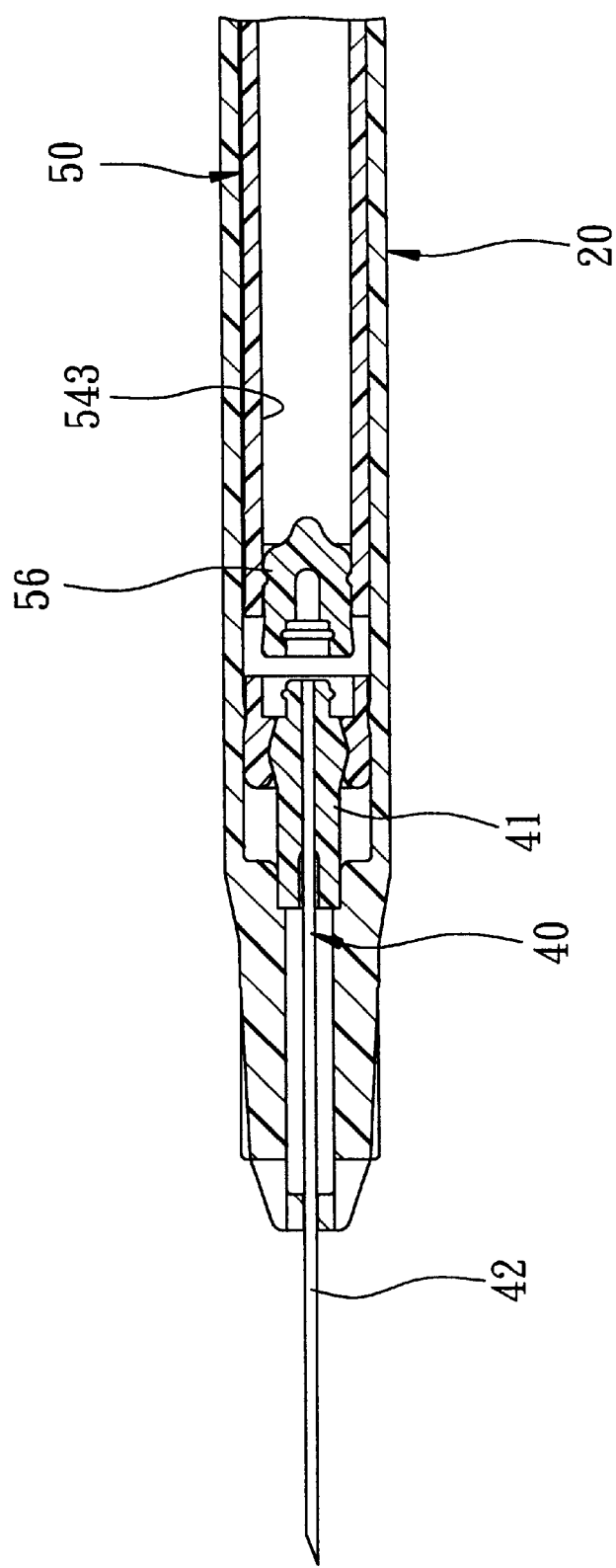
FIG. 21 is a fragmentary sectional view showing an alternate embodiment of a sealing member of a plunger of the disposable syringe of this invention.

The seal member 56 is disposed to be sealingly attached to the inner peripheral edge portion 543 at the top end wall 541 along an annular sealing line 566 so as to trap the fluid in the cavity 500 so as to maintain the reduced pressure (the substantially vacuum state in this embodiment). In the embodiment shown in FIG. 3, the seal member 56 is formed on the inner peripheral edge portion 543. Alternately, referring to FIG. 21, the sealing member 56 is disposed to be press-fitted to the inner peripheral edge portion 543 so as to form a sealing region. The seal member 56 has an engaging recess 563 which confronts the anchoring portion 412 and which extends in the longitudinal direction, and a third retaining groove 565 which is disposed in a front side of the engaging recess 563 and which extends in a radial direction relative to the axis (X), as shown in FIG. 5.

In use, the plunger 50 is pressed forwardly by a pushing force applied to the end cap 57 to push the surrounding sealing ring 59 to reach the rear surrounding edge portion 34 until the injection limiting protrusion 545 abuts against the injection limiting protrusion 25 to indicate the completion of the injection course. In this state, the anchoring portion 412 is retained in the engaging recess 563 by engagement of the third retaining protrusion 415 and the third retaining groove 565, thereby resulting in securing the needle seat 41 to the seal member 56.

Figure 6:
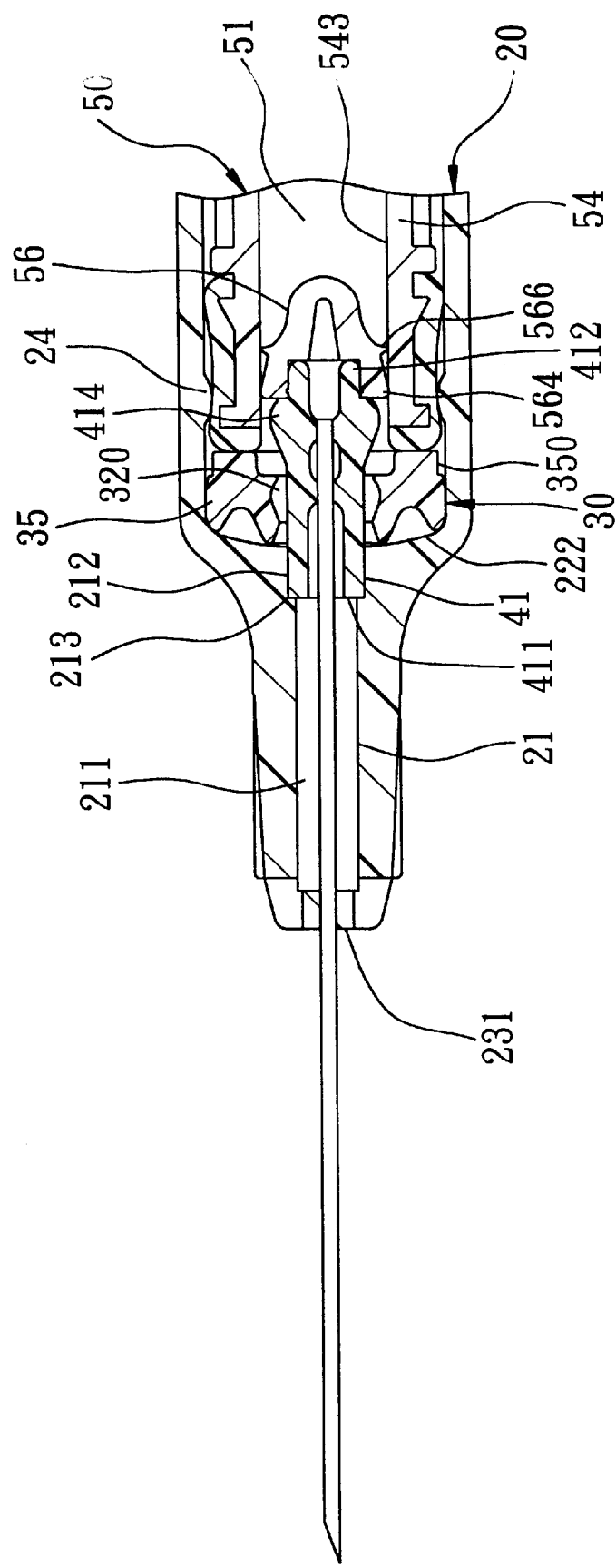
FIG. 6 is a sectional view showing the portion of the first preferred embodiment after use.
Figure 7:
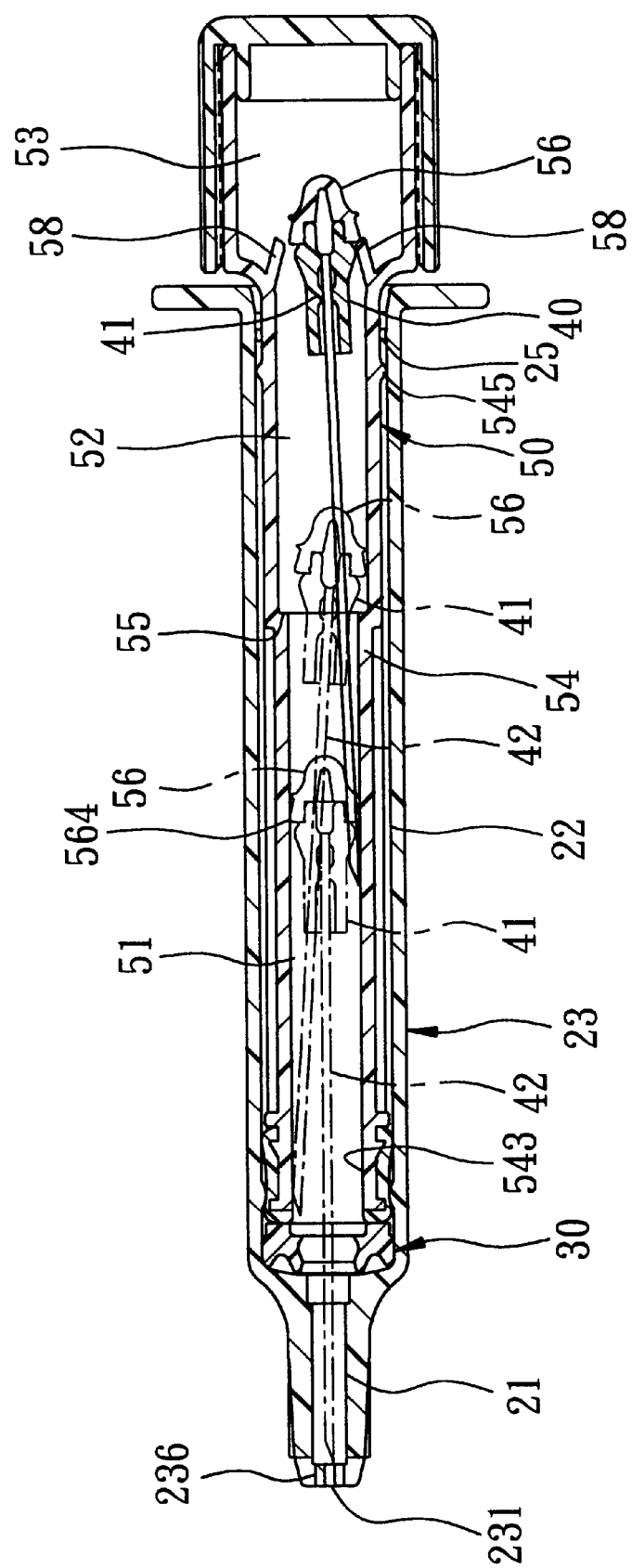
FIG. 7 is a sectional view of the first preferred embodiment, showing a needle cannula in a retracted state.

Subsequently, with reference to FIGS. 5 and 6, when a pushing force greater than the first and second frictional forces, i.e. frictional forces generated between the first retaining protrusion and groove 24,350 and between the second retaining protrusion and groove 414,320, is further applied to the end cap 57, the tubular barrier member 30 is pushed to move towards the surrounding shoulder portion 222 to force the second retaining groove 320 to disengage from the second retaining protrusion 414, so that the anchoring portion 412, which remains fixedly in place due to abutment of the surrounding front end wall 411 against the surrounding abutment wall 213, is exposed to and is impacted by an impact force from the seal member 56 along the axis (X) that the sealing line 566 is ruptured. Thus, the seal member 56 is released from the plunger body 54, and the needle seat 41 and the needle cannula 42, together with the seal member 56, are suctioned into the cavity 500 by a suction force resulting from a pressure difference between the ambient atmosphere and the reduced pressure in the cavity 500, as shown in FIG. 7. Note that the seal member 56 has an outer surrounding seal surface 564 which is configured to be kept in slidable contact and air-tight engagement with the inner peripheral edge portion 543 when the seal member 56 is suctioned in the front cavity segment 51. Moreover, by virtue of the shoulder portion 55 and the barrier ribs 58, the assembly of the needle seat 41, the needle cannula 42 and the seal member 56 can be trapped in the cavity 500.

Figure 8:
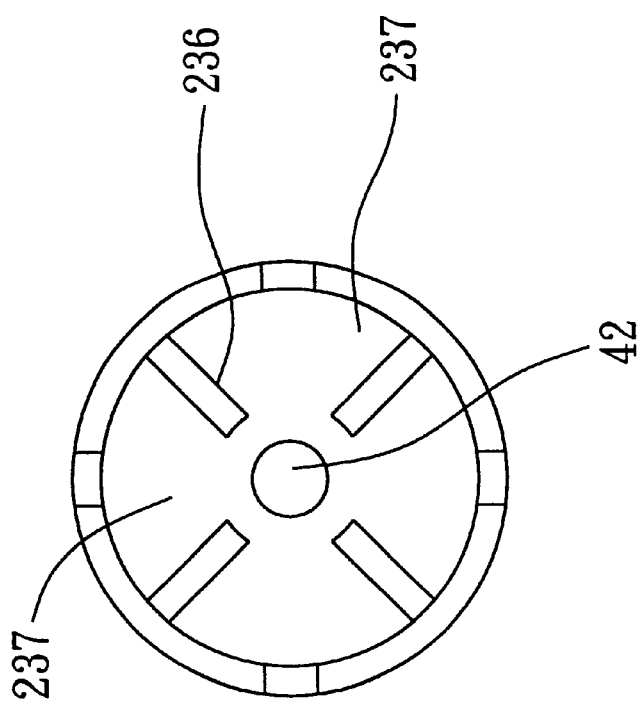
FIG. 8 is a cross-sectional view of a barrel shown in FIG. 5, taken along lines 8—8 thereof.

In addition, as shown in FIG. 8, the inner surrounding barrel wall surface of the barrel 20 is spaced apart from the needle cannula 42 in radial directions at the forward opening 231 to define a surrounding clearance therebetween. In particular, a plurality of ribs 237 are disposed on the inner surrounding barrel wall surface and are angularly displaced from one another. Each rib 237 extends toward the needle cannula 42 while forming an air duct 236 between two adjacent ones of the ribs 237 to communicate the passage of the barrel 20 with the ambient atmosphere. As such, the air ducts 236 can facilitate inflow of the ambient air into the cavity 500.

Figure 9:
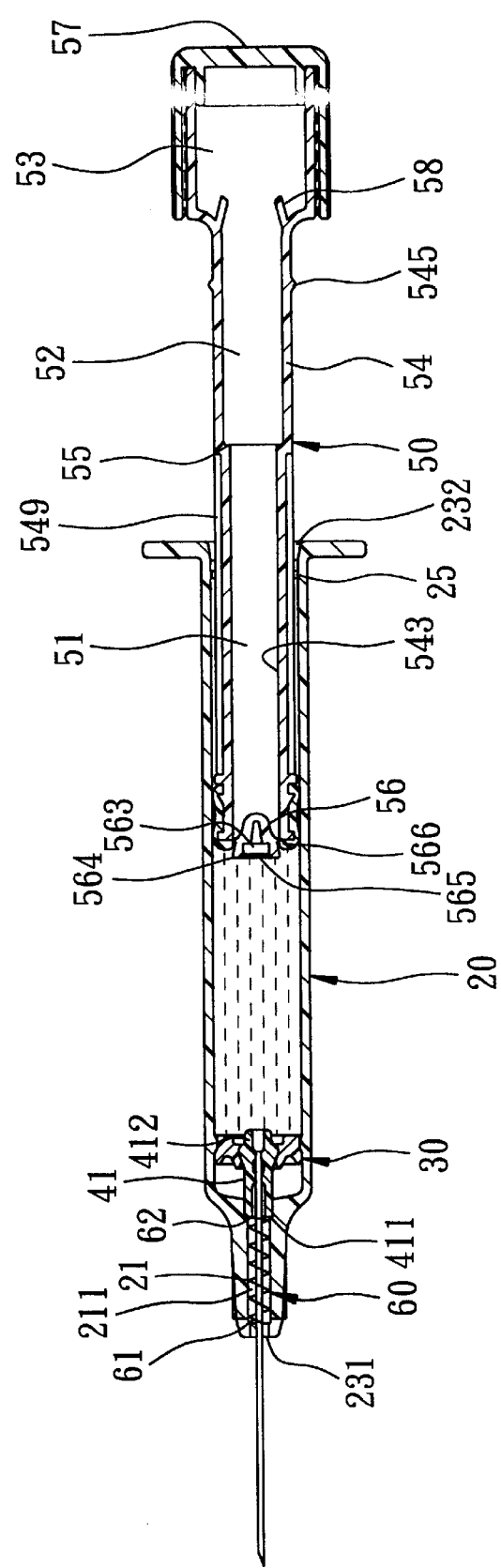
FIG. 9 is a sectional view of a second preferred embodiment of the disposable syringe according to this invention.
Figure 10:
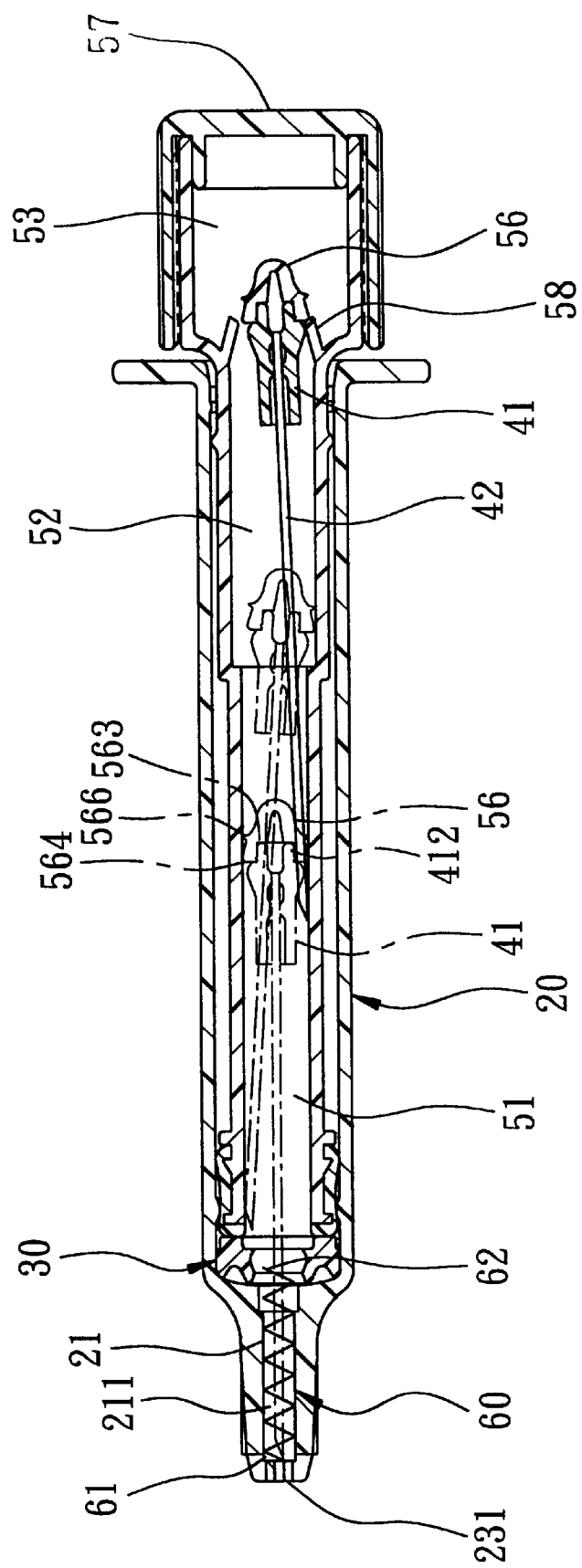
FIG. 10 is a sectional view of the second preferred embodiment, showing a needle cannula in a retracted state.

Referring to FIGS. 9 and 10, the second preferred embodiment of the disposable syringe according to this invention is shown to be similar to the aforesaid embodiment in construction. The disposable syringe of this embodiment further includes a biasing member 60, such as a compression spring, which is disposed in the front surrounding region 211 to bias the needle seat 41 toward the seal member 56. The biasing member 60 has two ends 61,62 abutting against the inner surrounding barrel wall surface at the forward opening 231 and the surrounding front end wall 411, respectively, so as to increase the impact force to facilitate retraction action of the suctioned assembly into the cavity 500.

Figure 11:
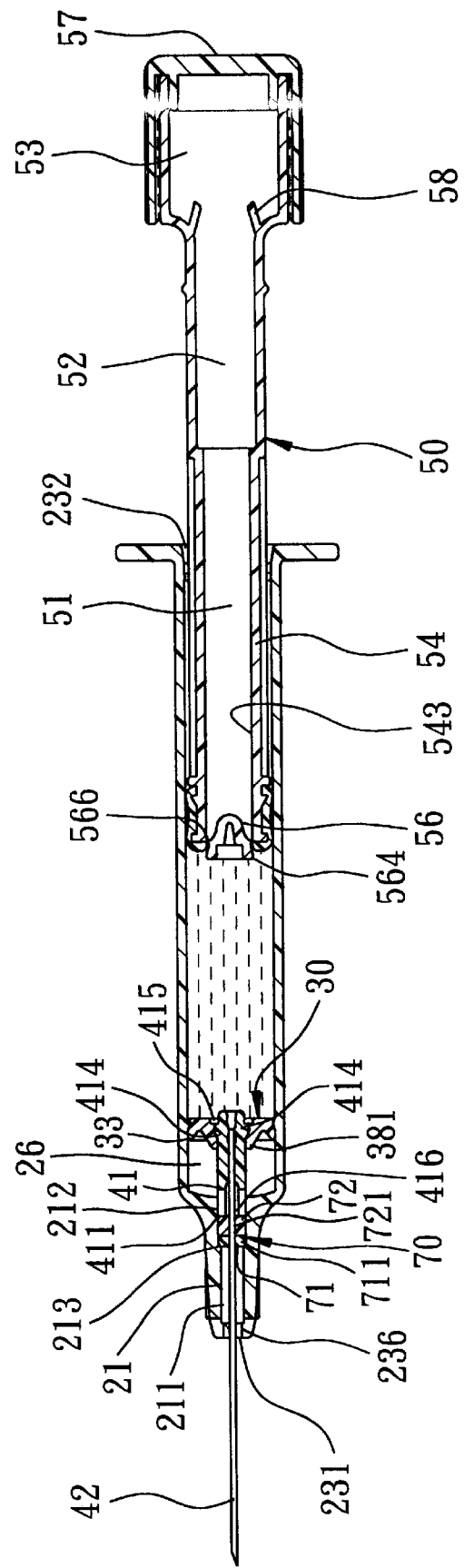
FIG. 11 is a sectional view of a third preferred embodiment of the disposable syringe according to this invention.
Figure 12:
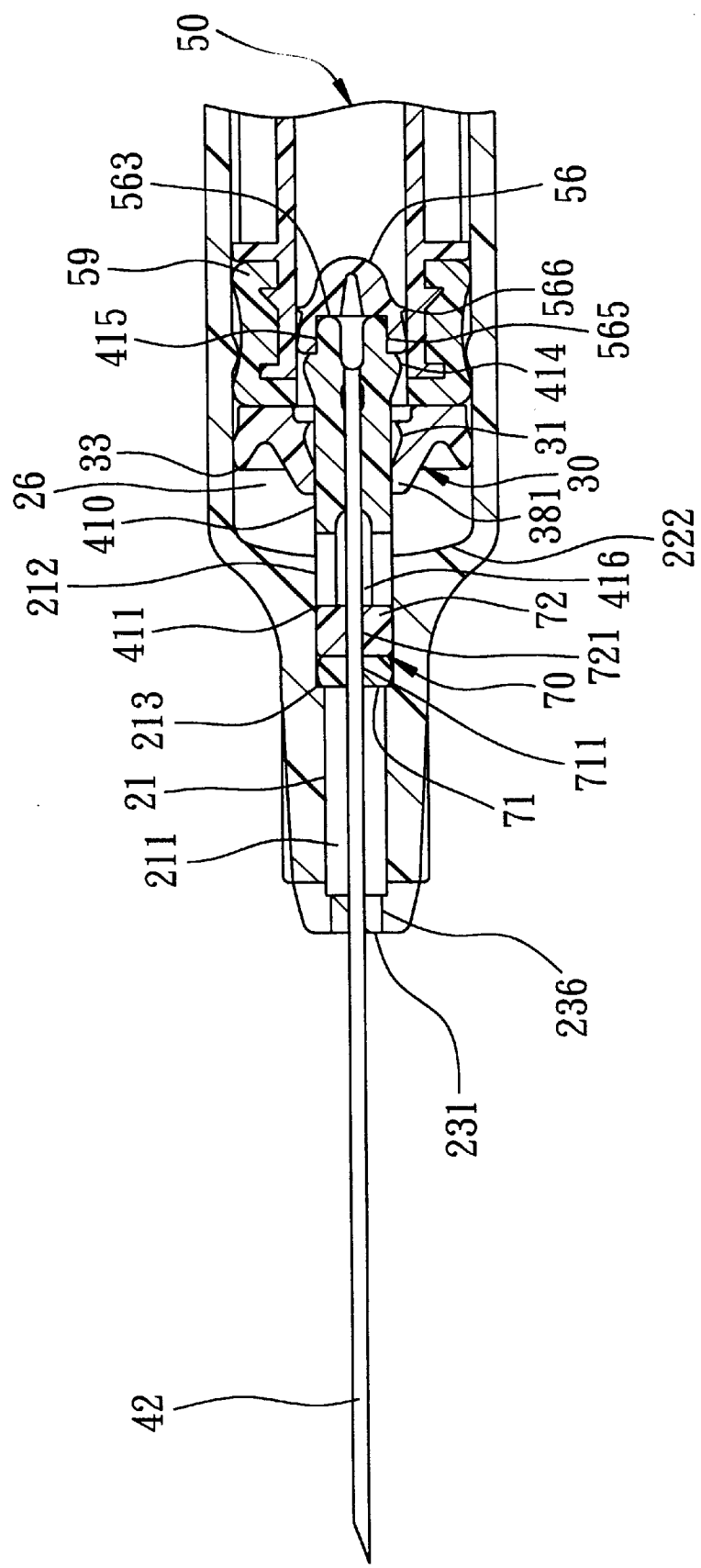
FIG. 12 is a sectional view showing a portion of the third preferred embodiment in detail.
Figure 13:
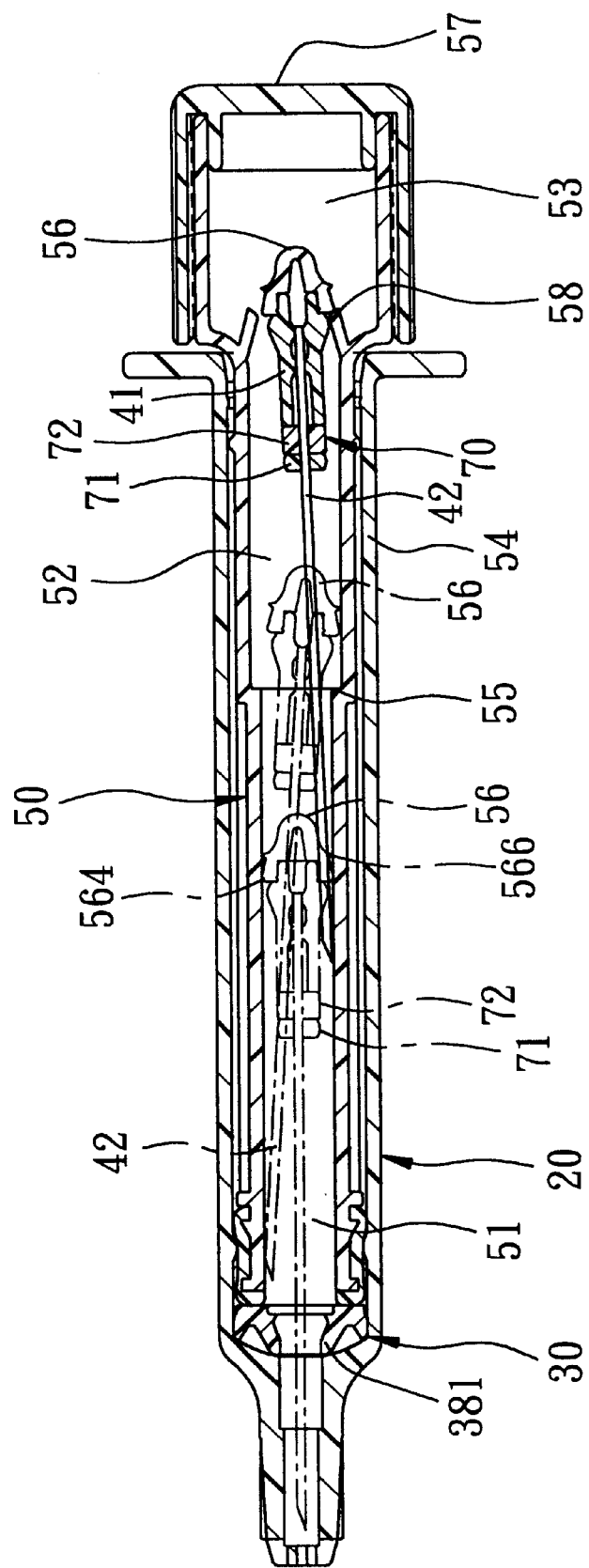
FIG. 13 is a sectional view of the third preferred embodiment, showing a needle cannula in a retracted state.

Referring to FIGS. 11, 12 and 13, the third preferred embodiment of the disposable syringe according to this invention is shown to be similar to the first preferred embodiment in construction. In this embodiment, the surrounding front end wall 411 includes a sealing member 70 which abuts against the surrounding abutment wall 213 and which is in air-tight engagement with the rear surrounding region 212 so as to maintain air-tightness of the compressible chamber 26. The sealing member 70 includes an elastomeric plate 71 and an elastomeric ring 72 which abut against each other and which have axial holes 711,721 that extend along the axis (X) to engage fittingly the needle cannula 42 therein. In addition, the inner barrier wall surface 31 of the tubular barrier member 30 further extends from the front surrounding edge portion 33 to have a deformable sealing portion 381 which is in air-tight engagement with the hub portion 410 of the tubular needle seat 41.

The compressible chamber 26 is filled with fluid. The hub portion 410 of the tubular needle seat 41 has a plurality of through holes 416 which are formed therethrough to be in fluid communication with the compressible chamber 26 and which extend in the longitudinal direction. As such, when the tubular barrier member 30 is moved towards the surrounding shoulder portion 222, the fluid is compressed to flow into the through holes 416, thereby helping force the anchoring portion 412 to move toward the seal member 56 so as to increase the impact force.

Figure 14:
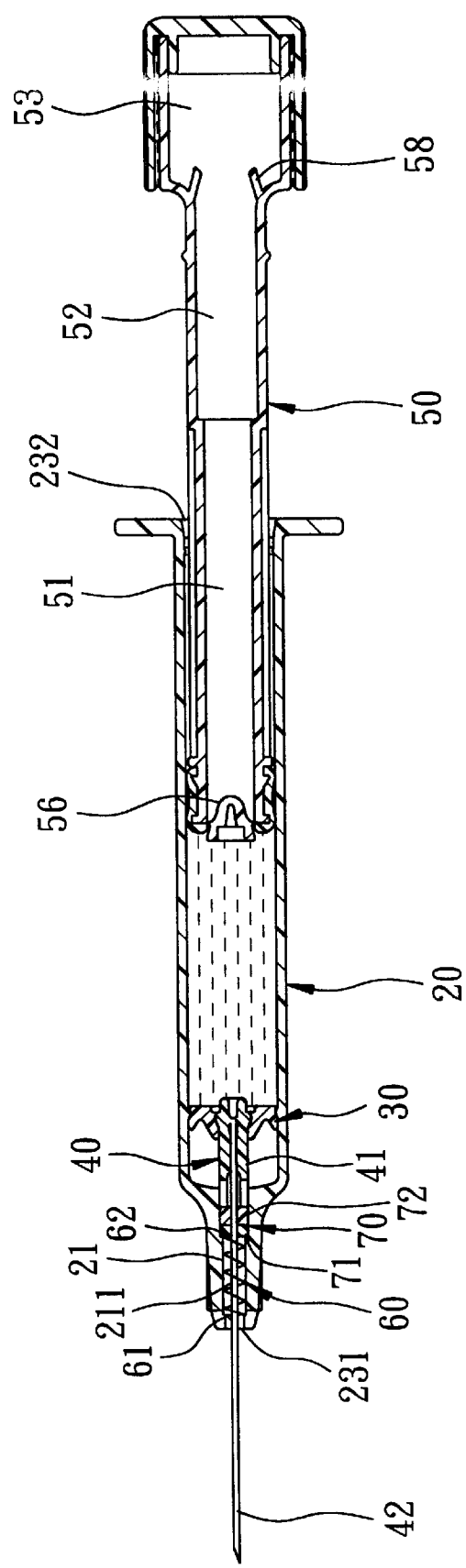
FIG. 14 is a sectional view of a fourth preferred embodiment of the disposable syringe according to this invention.
Figure 15:
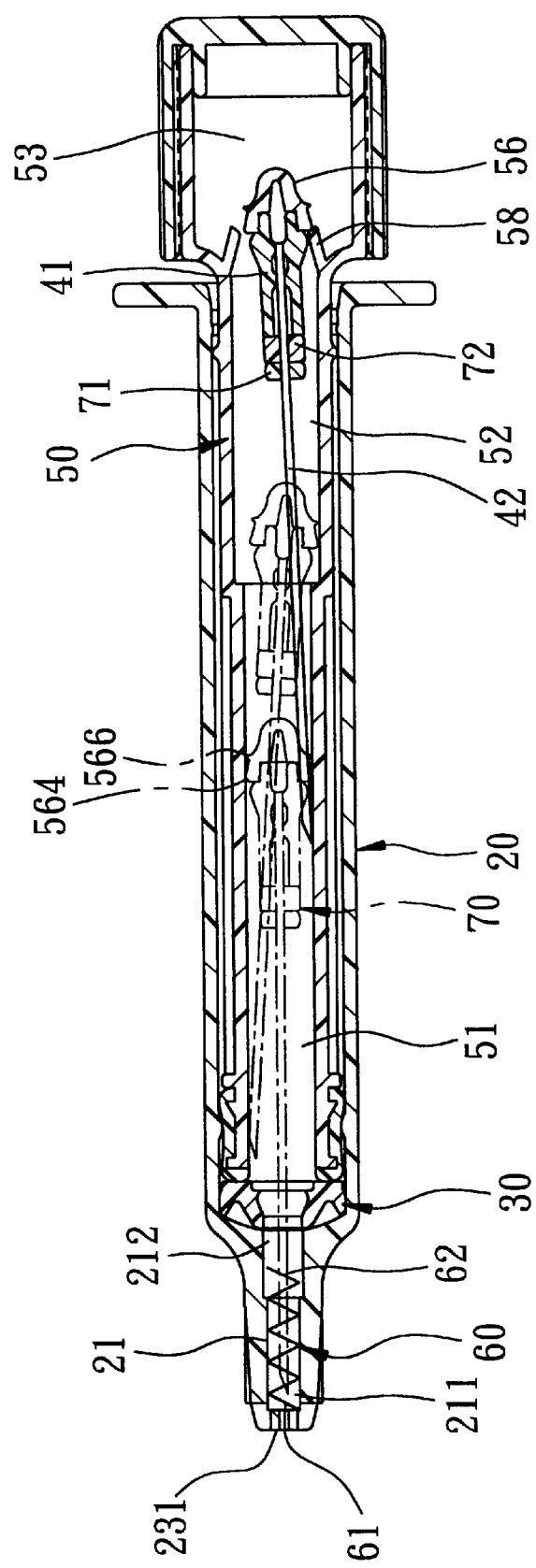
FIG. 15 is a sectional view of the fourth preferred embodiment, showing a needle cannula in a retracted state.
Figure 16:
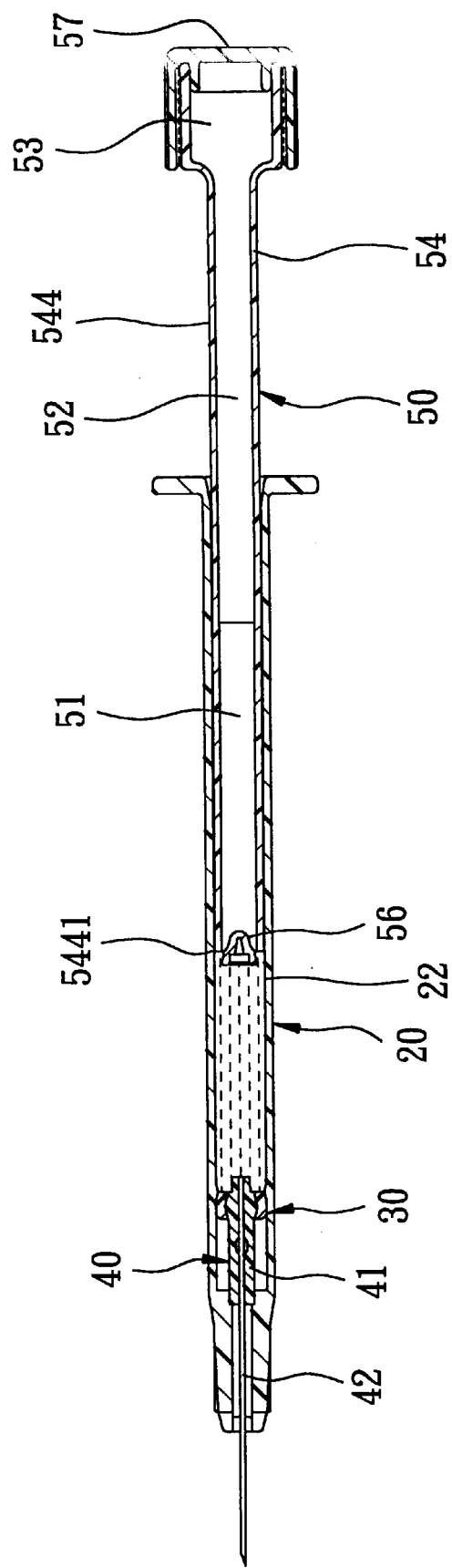
FIG. 16 is a sectional view of a fifth preferred embodiment of the disposable syringe according to this invention.
Figure 17:
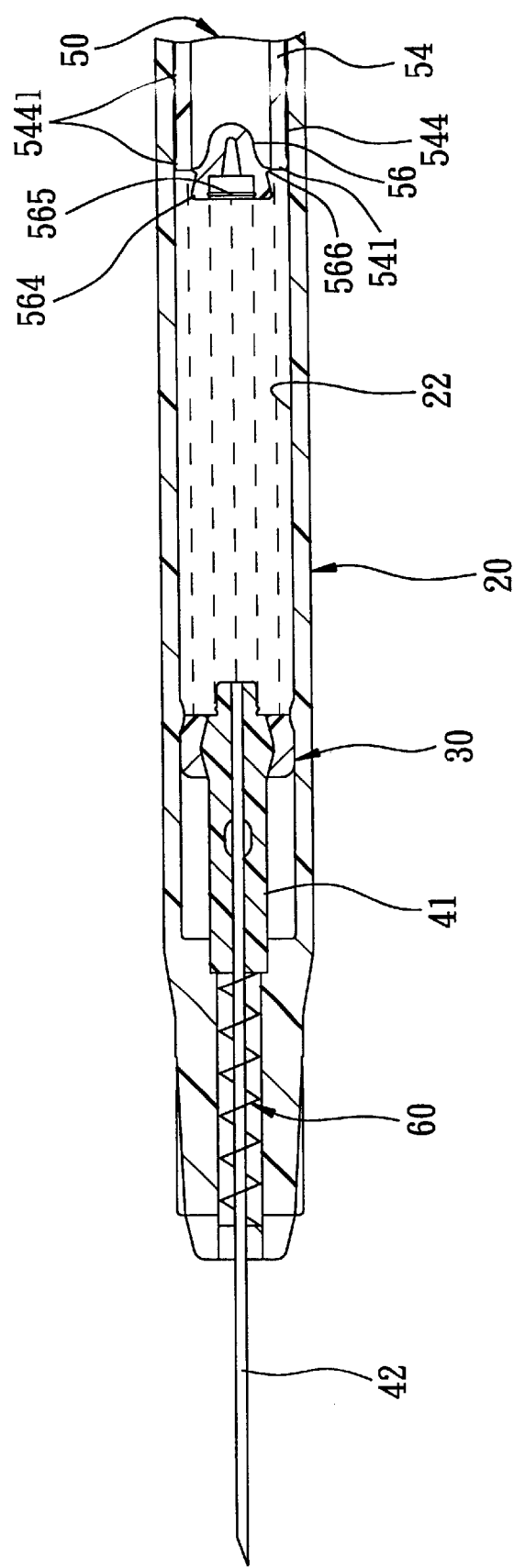
FIG. 17 is a fragmentary sectional view of a sixth preferred embodiment of the disposable syringe according to this invention.
Figure 18:
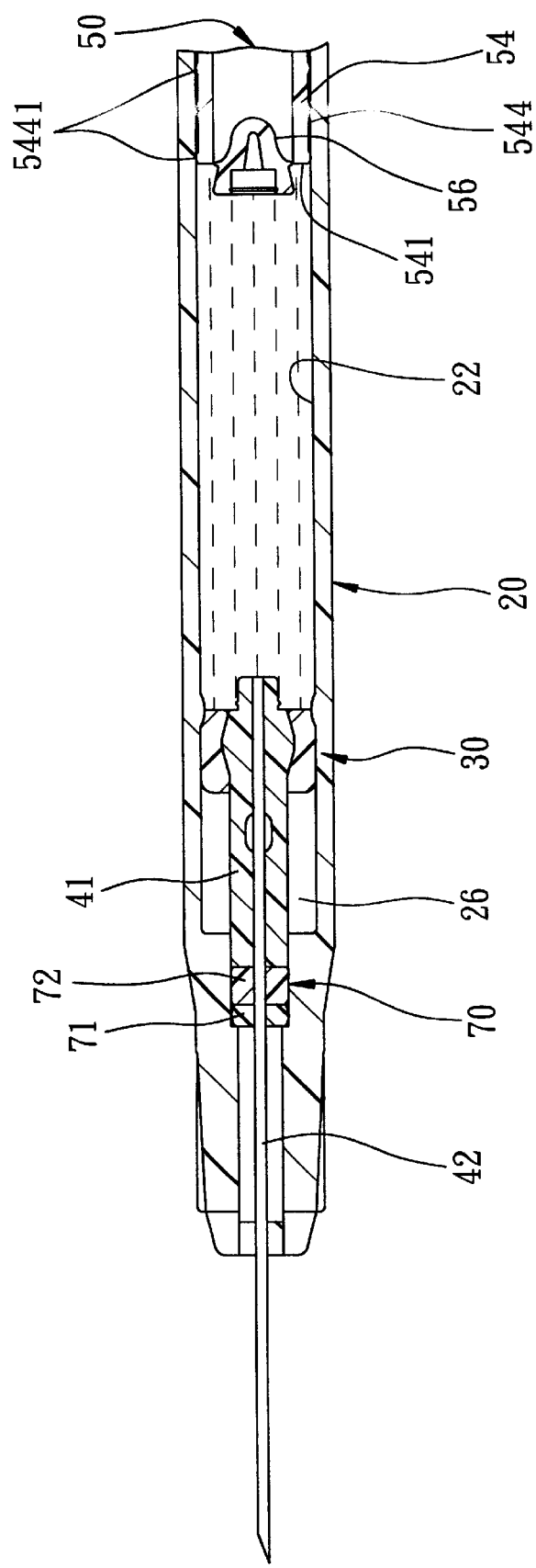
FIG. 18 is a fragmentary sectional view of a seventh preferred embodiment of the disposable syringe according to this invention.
Figure 19:
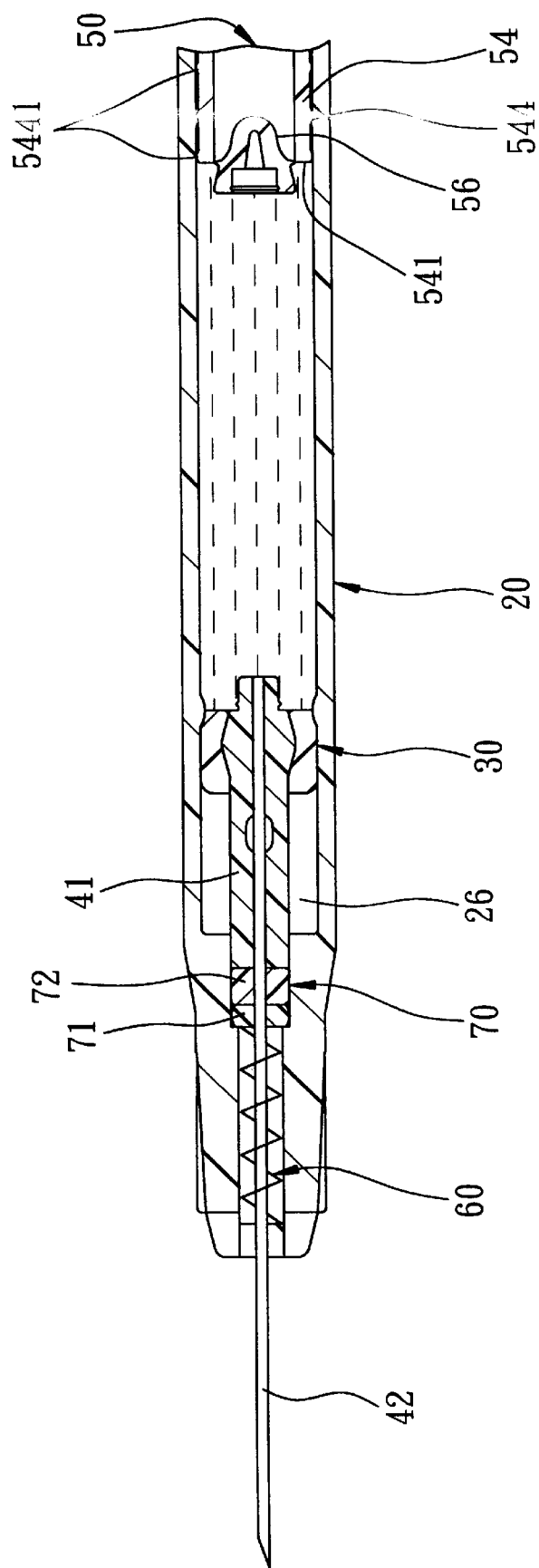
FIG. 19 is a fragmentary sectional view of an eighth preferred embodiment of the disposable syringe according to this invention.

Referring to FIGS. 14 and 15, the fourth preferred embodiment of the disposable syringe according to this invention is shown to be similar to the third preferred embodiment in construction, and further includes a biasing member 60 similar to that of the second preferred embodiment to bias the needle seat 41 toward the seal member 56. The biasing member 60 has two ends 61,62 abutting against the inner surrounding barrel wall surface at the forward opening 231 and the elastomeric plate 71 of the sealing member 70, respectively, so as to increase the impact force to facilitate retraction action of the suctioned assembly into the cavity 500.

Referring to FIGS. 16, 17, 18 and 19, the fifth, sixth, seventh and eighth preferred embodiments of the disposable syringe according to this invention are shown to be respectively similar to the first, second, third and fourth preferred embodiment in construction, but are used for an extremely small injection volume, such as 1 ml. Thus, the barrel 20, the tubular-barrier member 30, the needle assembly 40, the plunger 50 and the biasing member 60 are comparatively smaller. In addition, in stead of a separate surrounding sealing ring 59, the surrounding sealing ring in these embodiments includes a plurality of ring portions 5441 which are formed integrally with the outer peripheral wall surface 544 adjacent to the top end wall 541 for slidable and air-tight engagement with the larger-diameter segment 22. Therefore, the annular anchoring protrusion 546 and the annular retaining flange 547 (see FIG. 3) may be eliminated.

Figure 20:
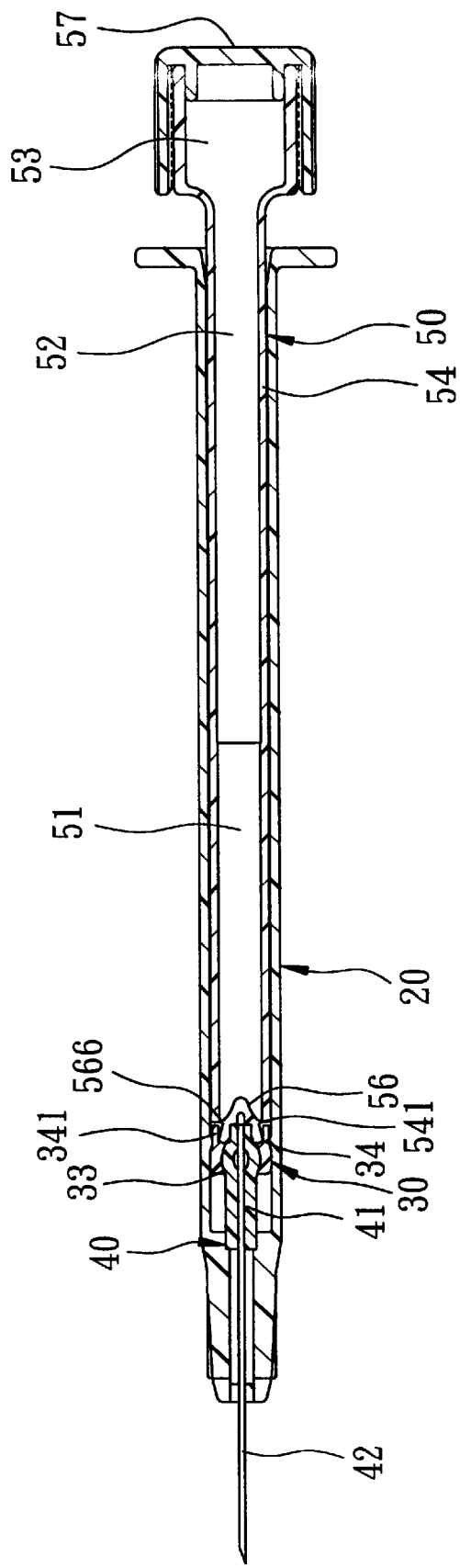
FIG. 20 is a sectional view of a ninth preferred embodiment of the disposable syringe according to this invention.

As shown in FIG. 20, the ninth preferred embodiment of the disposable syringe according to this invention is shown to be similar to the fifth preferred embodiment in construction. In this embodiment, the tubular barrier member 30 further includes an annular flange 341 which extends from the rear surrounding edge portion 34 and which is configured to be inserted into a clearance between the top end wall 541 of the plunger body 54 and the rear surrounding edge portion 34, thereby preventing trapping of medicine within the clearance.

As illustrated, the disposable syringe of this invention has the following advantages:

1. The suction of the tubular needle seat 41 and the needle cannula 42 occurs after the top end wall 541, the surrounding sealing ring 59, the seal member 56 and the tubular barrier member 30 are in tight contact with the tubular needle seat 41. Thus, the clearance may not exist therebetween to minimize trapping of medicine or blood within the barrel 20 after use.

2. By virtue of the first and second frictional forces and the abutment of the surrounding front end wall 411 against the surrounding abutment wall 213, the tubular needle seat 41 can be retained firmly in the retaining area during use. In addition, once the tubular needle seat 41 is released from the tubular barrier member 30 by a pushing force applied to the tubular barrier member 30, the tubular needle seat 41 can be suctioned smoothly and easily into the cavity 500.

3. After use, the needle seat 41 and the needle cannula 42 can be retracted into the cavity 500 of the plunger body 54 without the application of a pulling force to the plunger 50. Thus, the plunger body 54 can remain in the rear passageway 221 of the barrel 20, thereby facilitating the disposal of the disposable syringe.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe, comprising:
    a needle cannula;
    a barrel having an inner surrounding barrel wall surface which surrounds an axis and which confines a passage, said passage having rearward and forward openings which are disposed opposite to each other in a longitudinal direction parallel to the axis, said inner surrounding barrel wall surface including a larger-diameter segment and a smaller-diameter segment which confine rear and front passageways, respectively, and which are disposed proximate to said rearward and forward openings, respectively, to form a surrounding shoulder portion therebetween, said smaller-diameter segment including a front surrounding region and a rear surrounding region which is proximate to said surrounding shoulder portion and which is of a larger dimension than that of said front surrounding region so as to form a surrounding abutment wall therebetween, said larger-diameter segment including proximate and distal surrounding regions opposite to each other in the longitudinal direction and respectively proximate to and distal from said surrounding shoulder portion, said proximate surrounding region having a retaining area which is spaced apart from said surrounding shoulder portion in the longitudinal direction;
    a tubular barrier member which includes front and rear surrounding edge portions opposite to each other in the longitudinal direction and which includes inner and outer barrier wall surfaces opposite to each other and surrounding the axis, said outer barrier wall surface, in a position of use, being retained at said retaining area by virtue of a first frictional force generated therebetween while in water-tight engagement with said proximate surrounding region, thereby partitioning said rear passageway into a compressible chamber which confronts said surrounding shoulder portion, and an accommodation chamber which confronts said rear surrounding edge portion, said inner barrier wall surface having a grip segment;
    a tubular needle seat including
        a hub portion which is disposed to fix said needle cannula therein, and which has a surrounding front end wall extending radially relative to the axis,
        a surrounding gripped portion which extends from said hub portion in the longitudinal direction and away from said surrounding front end wall, and which is retained at said grip segment by virtue of a second frictional force generated between said surrounding gripped portion and said grip segment when said surrounding front end wall abuts against said surrounding abutment wall and when said needle cannula is disposed outwardly of said forward opening, and
        an anchoring portion extending from said surrounding gripped portion in the longitudinal direction and away from said hub portion; and
    a plunger which, in the use position, is disposed to be movable in said accommodation chamber, said plunger including
        a plunger body which includes a top end wall disposed movably to abut against said rear surrounding edge portion of said tubular barrier member, and a bottom end wall disposed opposite to said top end wall in the longitudinal direction and extending outwardly of said rearward opening so as to be manually operable, said top end wall having an inner peripheral edge portion which surrounds the axis and which defines a cavity therein, said cavity extending along the axis and towards said bottom end wall to contain a fluid at a reduced pressure, and a seal member disposed to be sealingly attached to said inner peripheral edge portion along a sealing line so as to trap said fluid in said cavity, said sealing line being configured such that when a pushing force greater than the first and second frictional forces, is manually applied to said bottom end wall to move said top end wall to abut against said rear surrounding edge portion of said tubular barrier member, said tubular barrier member is pushed to move towards said surrounding shoulder portion to force said grip segment to disengage from said surrounding gripped portion, so that said anchoring portion, which remains fixedly in place due to abutment of said surrounding front end wall against said surrounding abutment wall, is exposed to and is impacted by an impact force from said seal member along the axis so that said sealing line is ruptured, thereby releasing said seal member from said plunger body, and thereby permitting said tubular needle seat to be forced into engagement with said seal member to be subsequently suctioned into said cavity due to a pressure difference between the ambient atmosphere and the reduced pressure.

2. The disposable syringe of claim 1, wherein said barrel has an outer surrounding barrel wall surface which has a rib portion extending in the longitudinal direction and disposed at said front surrounding region adjacent to said forward opening, said disposable syringe further comprising a tip protector which has a sleeve end disposed to sleeve on said outer surrounding barrel wall surface, said sleeve end including a groove portion which mates with said rib portion to result in a splined engagement between said tip protector and said outer surrounding barrel wall surface, thereby ensuring secure shielding of said needle cannula.

3. The disposable syringe of claim 1, wherein one of said proximate surrounding region in said retaining area and said outer barrier wall surface is formed with a first retaining groove, and the other one of said proximate surrounding region in said retaining area and said outer barrier wall surface is formed with a first retaining protrusion which engages retainingly said first retaining groove to generate the first frictional force when said outer barrier wall surface is in the position of use, and wherein one of said grip segment of said inner barrier wall surface and said surrounding gripped portion of said tubular needle seat is a second retaining groove, and the other one of said grip segment of said inner barrier wall surface and said surrounding gripped portion of said tubular needle seat is a second retaining protrusion which engages retainingly said second retaining groove to generate the second frictional force when said surrounding front end wall abuts against said surrounding abutment wall.

4. The disposable syringe of claim 3, wherein said surrounding front end wall includes a sealing member which is in air-tight engagement with said rear surrounding region so as to maintain air-tightness of said compressible chamber, said compressible chamber being filled with a fluid, said hub portion of said tubular needle seat having a plurality of through holes which are distal from said surrounding front end wall in the longitudinal direction, which are formed therethrough to be in fluid communication with said compressible chamber, and which extend in the longitudinal direction such that when said tubular barrier member is moved towards said surrounding shoulder portion, said fluid is forced to flow into said through holes, thereby enforcing said anchoring portion to move toward said cavity so as to increase the impact force.

5. The disposable syringe of claim 4, wherein said sealing member is made from an elastomeric material, and has an axial hole extending along the axis to engage fittingly said needle cannula therein.

6. The disposable syringe of claim 4, wherein said inner barrier wall surface is formed with a deformable sealing portion which is in air-tight engagement with said hub portion of said tubular needle seat.

7. The disposable syringe of claim 1, further comprising a biasing member disposed in said front surrounding region to bias said tubular needle seat toward said seal member.

8. The disposable syringe of claim 4, further comprising a biasing member disposed in said front surrounding region to bias said tubular needle seat toward said seal member.

9. The disposable syringe of claim 3, wherein said front surrounding edge portion has a surrounding groove surrounding the axis so that said inner barrier wall surface more is deformable in radial directions relative to the axis.

10. The disposable syringe of claim 3, wherein said inner barrier wall surface is divergent from said grip segment to said front surrounding edge portion to prevent friction contact between said inner barrier wall surface and said hub portion of said tubular needle seat when said tubular needle seat is suctioned into said cavity.

11. The disposable syringe of claim 1, wherein said plunger body has a surrounding sealing ring which is disposed adjacent to said top end wall, which surrounds the axis, and which is slidable on and in air-tight engagement with said larger-diameter segment of said inner surrounding barrel wall surface.

12. The disposable syringe of claim 1, wherein said seal member has an engaging recess which confronts said anchoring portion and which extends in the longitudinal direction so as to engage said anchoring portion when said seal member is released from said plunger body, and a third retaining groove which is disposed in said engaging recess and which extends in a radial direction relative to the axis, said anchoring portion having a third retaining protrusion which is disposed to be retained in said third retaining groove when said anchoring portion engages said engaging recess such that said seal member, together with said tubular needle seat, is suctioned into said cavity.

13. The disposable syringe of claim 12, wherein said cavity includes front and rear cavity segments which are disposed proximate to said top and bottom end walls, respectively, and which have smaller and larger inner diameters, respectively, said seal member having an outer surrounding seal surface which is configured to be kept in slidable contact and air-tight engagement with said inner peripheral edge portion when said seal member is suctioned in said front cavity segment.

14. The disposable syringe of claim 13, wherein said plunger further includes a plurality of barrier ribs, each of which is disposed adjacent to said bottom end wall and which extends from said inner peripheral edge portion radially and toward the axis so as to trap said tubular needle seat when said tubular needle seat is forced towards said bottom end wall.

15. The disposable syringe of claim 13, wherein said plunger body further includes an outer peripheral wall surface, and a plurality of rib plates which are formed on said outer peripheral wall surface at said front cavity segment, and which are flush with said outer peripheral wall surface at the rear cavity segment.

16. The disposable syringe of claim 1, wherein said inner surrounding barrel wall surface is spaced apart from said needle cannula in radial directions relative to the axis at said forward opening to define a surrounding clearance therebetween.

17. The disposable syringe of claim 16 further comprising a plurality of ribs which are disposed on said inner surrounding barrel wall surface and which are angularly displaced from one another, each of said ribs extending towards said needle cannula, an air duct being formed between two adjacent ones of said ribs to communicate said passage with the ambient atmosphere.

18. The disposable syringe of claim 1, further comprising two injection limiting protrusions which are disposed on said plunger body adjacent to said bottom end wall and said larger-diameter segment adjacent to said rearward opening respectively, and which abut against each other when said top end wall reaches said rear surrounding edge portion so as to limit an extent of an injection course.

19. The disposable syringe of claim 1, wherein said bottom end wall has an opening which is in fluid communication with said cavity, said plunger further including an end cap which is disposed to cover said opening and to be in air-tight engagement with said bottom end wall.

20. A disposable syringe, comprising:

a needle cannula;

a barrel having an inner surrounding barrel wall surface which surrounds an axis and which confines a passage, said passage having rearward and forward openings which are disposed opposite to each other in a longitudinal direction parallel to the axis, said inner surrounding barrel wall surface including a larger-diameter segment and a smaller-diameter segment which confine rear and front passageways, respectively, and which are disposed proximate to said rearward and forward openings, respectively, to form a surrounding shoulder portion therebetween, said smaller-diameter segment including a front surrounding region and a rear surrounding region which is proximate to said surrounding shoulder portion and which is of a larger dimension than that of said front surrounding region so as to form a surrounding abutment wall therebetween, said larger-diameter segment including proximate and distal surrounding regions opposite to each other in the longitudinal direction and respectively proximate to and distal from said surrounding shoulder portion, said proximate surrounding region having a retaining area which is spaced apart from said surrounding shoulder portion in the longitudinal direction;

a tubular barrier member which includes front and rear surrounding edge portions opposite to each other in the longitudinal direction and which includes inner and outer barrier wall surfaces opposite to each other and surrounding the axis, said outer barrier wall surface, in a position of use, being retained at said retaining area by virtue of a first frictional force generated therebetween while in water-tight engagement with said proximate surrounding region, thereby partitioning said rear passageway into a compressible chamber which confronts said surrounding shoulder portion, and an accommodation chamber which confronts said rear surrounding edge portion, said inner barrier wall surface having a grip segment, said compressible chamber being filled with a fluid;

a tubular needle seat including a hub portion which is disposed to fix said needle cannula therein, and which has a surrounding front end wall extending radially relative to the axis, said surrounding front end wall including a sealing member which is in air-tight engagement with said rear surrounding region, said inner barrier wall surface of said tubular barrier member being formed with a deformable sealing portion which is in air-tight engagement with said hub portion of said tubular needle seat so as to maintain air-tightness of said compressible chamber, said hub portion further having a plurality of through holes which extend from said surrounding front end wall in the longitudinal direction and which are formed therethrough to be in fluid communication with said compressible chamber;

a surrounding gripped portion which extends from said hub portion in the longitudinal direction and away from said surrounding front end wall, and which is retained at said grip segment by virtue of a second frictional force generated between said surrounding gripped portion and said grip segment when said sealing member abuts against said surrounding abutment wall and when said needle cannula is disposed outwardly of said forward opening, and an anchoring portion extending from said surrounding gripped portion in the longitudinal direction and away from said hub portion; and a plunger which, in the use position, is disposed to be movable in said accommodation chamber, said plunger including a plunger body which includes a top end wall disposed movably to abut against said rear surrounding edge portion of said tubular barrier member, and a bottom end wall disposed opposite to said top end wall in the longitudinal direction and extending outwardly of said rearward opening so as to be manually operable, said top end wall having an inner peripheral edge portion which surrounds the axis and which defines a cavity therein, said cavity extending along the axis and towards said bottom end wall, and a seal member attached to said inner peripheral edge portion along a line, said sealing line being configured such that when a pushing force greater than the first and second frictional forces, is manually applied to said bottom end wall to move said top end wall to abut against said rear surrounding edge portion of said tubular barrier member, said tubular barrier member is pushed to move towards said surrounding shoulder portion to compress said fluid in said compressible chamber into said through holes, thereby generating a pressure force in the longitudinal direction on said surrounding gripped portion and forcing said grip segment to disengage from said surrounding gripped portion, so that said anchoring portion, which remains fixedly in place due to abutment of said sealing member against said surrounding abutment wall, is exposed to and is impacted by an impact force from said seal member along the axis such that said line is ruptured, thereby releasing said seal member from said plunger body, and thereby permitting said tubular needle seat to be forced by the pressure force into engagement with said seal member to be subsequently moved into said cavity.

* * * * *